United States Patent
Barth et al.

(10) Patent No.: US 9,782,139 B2
(45) Date of Patent: Oct. 10, 2017

(54) X-RAY DEVICE

(71) Applicant: SIEMENS AKTIENGESELLSCHAFT, Munich (DE)

(72) Inventors: Karl Barth, Hoechstadt (DE); Rainer Graumann, Hoechstadt (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/779,099

(22) PCT Filed: Feb. 3, 2014

(86) PCT No.: PCT/EP2014/051982
§ 371 (c)(1),
(2) Date: Sep. 22, 2015

(87) PCT Pub. No.: WO2014/154382
PCT Pub. Date: Oct. 2, 2014

(65) Prior Publication Data
US 2016/0045177 A1 Feb. 18, 2016

(30) Foreign Application Priority Data

Mar. 27, 2013 (DE) ........................ 10 2013 205 494

(51) Int. Cl.
*A61B 6/00* (2006.01)
*A61N 5/10* (2006.01)
(Continued)

(52) U.S. Cl.
CPC .......... *A61B 6/4458* (2013.01); *A61B 6/4429* (2013.01); *A61B 6/4452* (2013.01);
(Continued)

(58) Field of Classification Search
CPC .. A61B 6/00; A61B 6/03; A61B 6/032; A61B 6/035; A61B 6/40; A61B 6/42;
(Continued)

(56) References Cited

U.S. PATENT DOCUMENTS 3,617,749 A * 11/1971 Massiot ............... A61B 6/4441
378/181
6,104,780 A * 8/2000 Hanover ............... A61B 6/4014
378/101
(Continued)

FOREIGN PATENT DOCUMENTS

DE 102011006122 A1 9/2012
DE 102011082075 A1 3/2013

*Primary Examiner* — Anastasia Midkiff
(74) *Attorney, Agent, or Firm* — Laurence Greenberg; Werner Stemer; Ralph Locher

(57) ABSTRACT

An X-ray device has a detector which is arranged on a mobile unit and is assigned to a first positioning unit. An X-ray source is arranged on an arcuate second positioning unit. The positioning of the first and second positioning units can be matched to one another in the course of their movements. The first positioning unit has at least one articulated arm and the second positioning unit has a first and a second arc-shaped positioning element. The first and second positioning units are arranged separately from one another on a movable unit.

16 Claims, 4 Drawing Sheets

(51) Int. Cl.
*B25J 9/06* (2006.01)
*B25J 19/02* (2006.01)
*A61B 6/03* (2006.01)
*A61B 50/26* (2016.01)
*B25J 9/00* (2006.01)

(52) U.S. Cl.
CPC ............ *A61B 6/587* (2013.01); *A61N 5/1083* (2013.01); *A61B 6/035* (2013.01); *A61B 6/4405* (2013.01); *A61B 6/4441* (2013.01); *A61B 50/26* (2016.02); *A61B 2560/0406* (2013.01); *A61B 2560/0437* (2013.01); *A61B 2560/0443* (2013.01); *B25J 9/009* (2013.01); *B25J 9/0009* (2013.01); *B25J 9/0087* (2013.01); *B25J 9/06* (2013.01); *B25J 19/027* (2013.01)

(58) Field of Classification Search
CPC ....... A61B 6/44; A61B 6/4405; A61B 6/4411; A61B 6/4429; A61B 6/4435; A61B 6/4441; A61B 6/4452; A61B 6/4458; A61B 6/58; A61B 6/587; A61B 50/00; A61B 50/20; A61B 50/24; A61B 50/26; A61B 2560/04; A61B 2560/0406; A61B 2560/0437; A61B 2560/0443; A61N 5/1083; H05G 1/00; H05G 1/02; H05G 1/04; H01J 37/00; H01J 37/02; H01J 37/023; B25J 5/00; B25J 5/007; B25J 9/00; B25J 9/0009; B25J 9/0087; B25J 9/009; B25J 9/06; B25J 9/08; B25J 18/00; B25J 18/005; B25J 19/00; B25J 19/02; B25J 19/027
See application file for complete search history.

(56) References Cited

U.S. PATENT DOCUMENTS

| | | | |
|---|---|---|---|
| 6,256,374 B1 * | 7/2001 | Tomasetti | A61B 6/464 378/198 |
| 6,325,537 B1 | 12/2001 | Watanabe | |
| 6,428,206 B1 | 8/2002 | Watanabe | |
| 6,619,840 B2 * | 9/2003 | Rasche | A61B 6/032 378/196 |
| 8,944,680 B2 | 2/2015 | Graumann | |
| 2003/0112926 A1 * | 6/2003 | Atzinger | A61B 6/4233 378/196 |
| 2008/0089468 A1 * | 4/2008 | Heigl | A61B 6/032 378/20 |
| 2010/0303207 A1 | 12/2010 | Tsujii et al. | |
| 2013/0223597 A1 * | 8/2013 | Graumann | A61B 6/4452 378/197 |
| 2014/0188132 A1 * | 7/2014 | Kang | A61B 6/4441 606/130 |
| 2015/0049862 A1 * | 2/2015 | Ancar | A61B 6/08 378/190 |
| 2015/0265237 A1 * | 9/2015 | Keeve | A61B 6/032 378/41 |

* cited by examiner

X-RAY DEVICE

BACKGROUND OF THE INVENTION

Field of the Invention

The invention relates to a mobile X-ray device.

Imaging methods, in particular X-ray imaging methods, are used, for example, for diagnostic purposes before and during a medical intervention and for monitoring purposes after a medical intervention. X-ray imaging methods are likewise used for planning purposes and for documenting the course of a disease. To be able to use the X-ray devices at any location, they are designed to be mobile. For individual X-ray images or a series of X-ray images, the mobile X-ray device is brought to the patient in order to create individual 2D X-ray images or a series of 2D X-ray images of partial regions thereof. The image data from a series of 2D X-ray images can be used for computation for 3D imaging. On account of the weight being reduced in order to provide mobility, a high degree of computing complexity is required in order to produce slice images and/or 3D images. Likewise, increased positioning and computing complexity is required if the aim is to produce an enlarged image of partial regions of an object.

The problem addressed by the invention is that of making available a further X-ray device in which, in addition to 2D images and/or a series of 2D images, it is possible to take slice images and/or 3D images.

The invention is solved by the features of the claimed invention.

BRIEF SUMMARY OF THE INVENTION

The subject matter of the invention is a mobile X-ray device which has a first positioning unit for a detector and a second positioning unit for an X-ray source. The first positioning unit is composed of at least one articulated arm and the second positioning unit is composed of at least one arc-shaped positioning element.

The invention affords the advantage that X-ray source and detector are freely positionable.

The invention affords the advantage that the detector and the X-ray source of the mobile X-ray device are each arranged on separately controllable positioning units.

The invention affords the advantage that the object that is to be X-rayed remains in the isocenter.

The invention affords the advantage that 2D images of any desired location of an object can be produced without increased time demands.

The invention affords the advantage that the direction of the X-ray beam tracks a detector that moves around an object, while the X-ray source remains stationary.

The invention affords the advantage of permitting compact operation by the detector-guided 2D X-ray imaging.

The invention affords the advantage of permitting a high degree of stability during a rapid spatial orientation of the X-ray source and of the detector in a series of 2D images for 3D computation.

The invention affords the advantage that, in a parked position, the X-ray source and the detector, which is secured on an articulated arm, are able to be positioned in a way that saves space.

The invention affords the advantage that the detector can be brought very close to an object that is to be X-rayed, and this object is viewable on the whole image region.

The invention affords the advantage that the mobile X-ray device has a low center of gravity.

The invention affords the advantage that a 3D image can be formed merely by double AP/PA (anterior posterior/posterior anterior) imaging.

The invention affords the advantage that, by means of articulated arms that can be designed like a telescope, it is possible to navigate all the way round an object.

The invention affords the advantage that the mobile X-ray device has a compact structure and can be parked under an operating table in a place where it does not get in the way.

The invention affords the advantage that it is also possible to take X-ray images that are inclined about a transverse axis of the table.

The invention affords the advantage that X-ray images can be taken and combined without parallax.

BRIEF DESCRIPTION OF THE SEVERAL VIEWS OF THE DRAWING

The invention is explained in more detail with reference to the attached figures, in which.

DESCRIPTION OF THE INVENTION

A mobile X-ray device has a detector, which is arranged on a movable unit and assigned to a first positioning unit, and an X-ray source, which is arranged on an arc-shaped second positioning unit.

Figure 1:
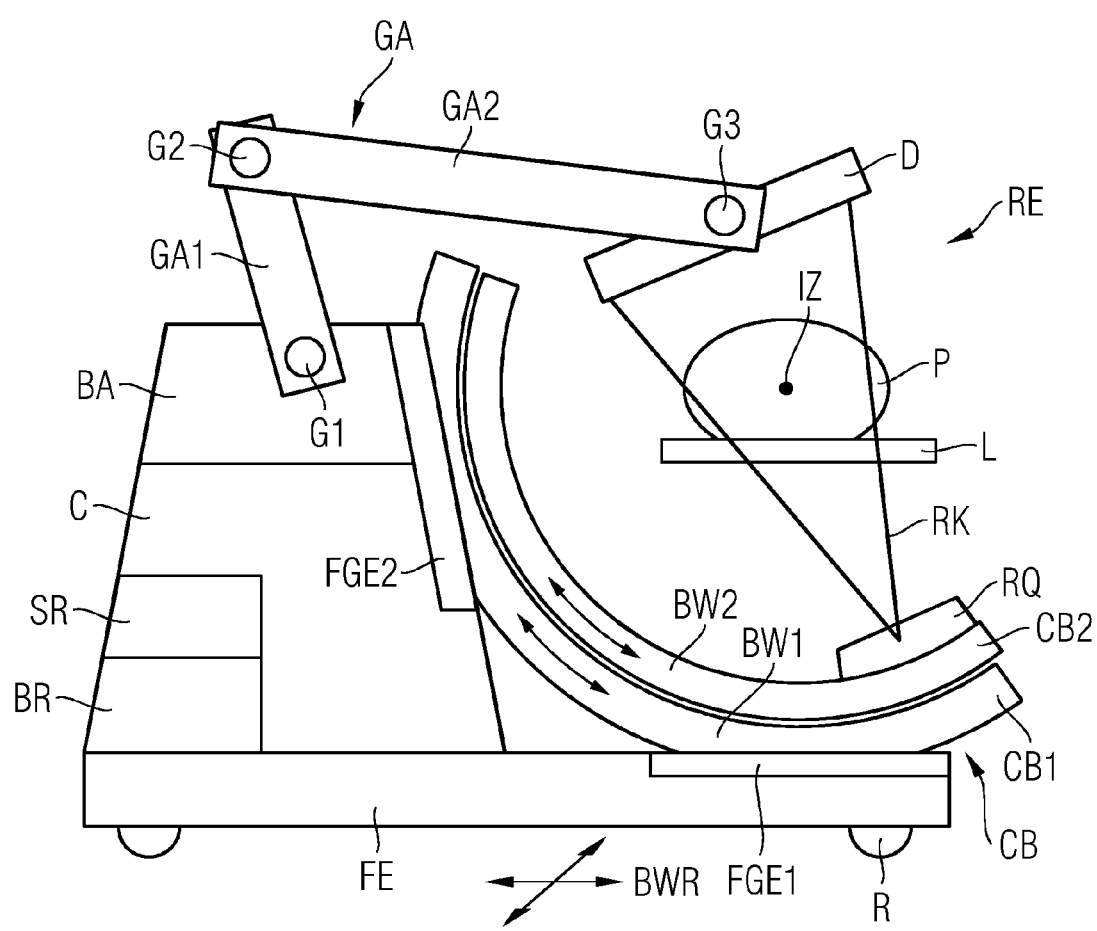
FIG. 1 shows a side view of the X-ray device.

A mobile X-ray device RE is shown in FIG. 1. For a detector D and an X-ray source RQ, the X-ray device RE has respective positioning units GA, CB, which are controllable independently of each other. The X-ray source RQ and the detector D can be controlled in orientation with each other. In the illustrated orientation, the X-ray cone RK emanating from the X-ray source RQ is detected by the detector D. The detector D is guided by a first positioning unit GA, and the X-ray source RQ is guided by a second positioning unit CB. The first and second positioning units GA, CB are designed in such a way that the detector D and the X-ray source RQ can be aligned with each other. The X-ray beam or X-ray cone RK of the X-ray source RQ can be moved, for X-ray images, around the object, tracking a rotary and/or orbital trajectory of the detector D. The mobile X-ray device RE has a movable unit FE. The latter is designed in such a way that a chassis C, receiving the first positioning unit GA, and first guide elements FGE1 for parts of the second positioning unit CB are arranged on it. Second guide elements FGE2 for guiding parts of the second positioning unit CB are arranged on the chassis C. On its underside, the movable unit FE is equipped with transport units, for example rollers or wheels R. The transport units can be controlled manually and/or electronically. A control computer, for control elements for positioning the first and second positioning units GA, CB, and an image computer BR, for processing 2D X-ray images and for computing a data volume, formed by a multiplicity of 2D X-ray images, to give slice images or a 3D representation of X-rayed objects, are provided in the chassis C. By means of the control computer SR, control signals relating to the park position and repositioning of the mobile X-ray device RE can be initiated. The first positioning unit GA is configured with a first and a second articulated arm GA1, GA2. The first and/or second articulated arm GA1, GA2 can have telescopic elements. The first articulated arm GA1 is connected to the chassis C via a first articulation G1, while the first articulated arm GA1 and the second articulated arm GA2 are connected by a second articulation G2, and the detector unit D is connected to a third articulation G3 at the free end of the second articulated arm GA2. The first, second and third articulations G1, G2, G3 are all lockable and each have at least one degree of freedom. The second positioning unit CB is configured with a first and a second positioning element CB1, CB2. The detector D is secured on the second articulated arm GA2, and the X-ray source RQ is secured on a second positionable element CB1, so as to be movable to all sides via controllable articulations. The first and second positioning elements CB1, CB2 of the second positioning unit CB are configured like arcs of a circle. The first positioning element CB1 forms a first, outer arc of a circle, and the second positioning element CB2 forms a second, inner arc of a circle. The first positioning element CB1 is guided and fixed on the chassis C at least by the first guide element FGE1 in the floor area of the movable unit FE and/or by the second guide element FGE2. The second positioning element CB2 lies in the first positioning element CB1 and is connected thereto via guide elements. The orientation of the first positioning element CB1 and of the second positioning element CB2 can take place along the indicated first and second directions of movement BW1 and BW2. The detector D can be oriented to match the orientation of the X-ray source RQ. The second positioning element CB2 can also be enclosed at least on three sides by the first positioning element CB1. The position of the X-ray source RQ arranged at/on the second positioning element CB2 can be obtained by telescopic deployment of the second positioning element CB2 from the first positioning element CB1.

The movable unit FE is equipped with rollers or wheels R. These rollers or wheels R are controllable via the control computer and via control electronics in such a way that a direction of travel for the X-ray unit RE can be predefined. The direction of travel can be assisted by sensors. Repositioning can be carried out by electromagnetic and/or optical navigation systems. Adjustment and orientation of the rollers or wheels R can be assisted by an electric motor drive. The directions of movement of the mobile X-ray unit RE are indicated by the directions of movement BWR. In addition to electronic adjustment of the direction of the rollers and/or wheels R, motor assistance is also provided in driving the rollers and/or wheels R for transporting the X-ray device RE from and to a site of use.

Figure 2:
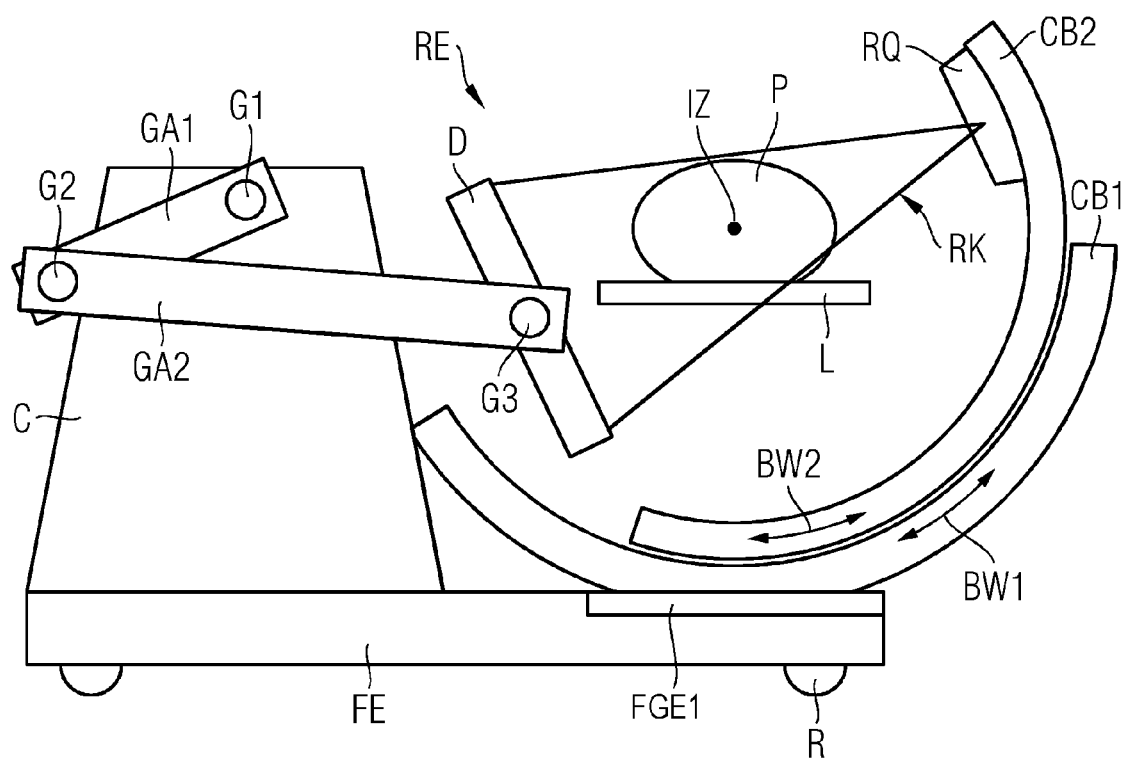
FIG. 2 shows a further side view.
Figure 3:
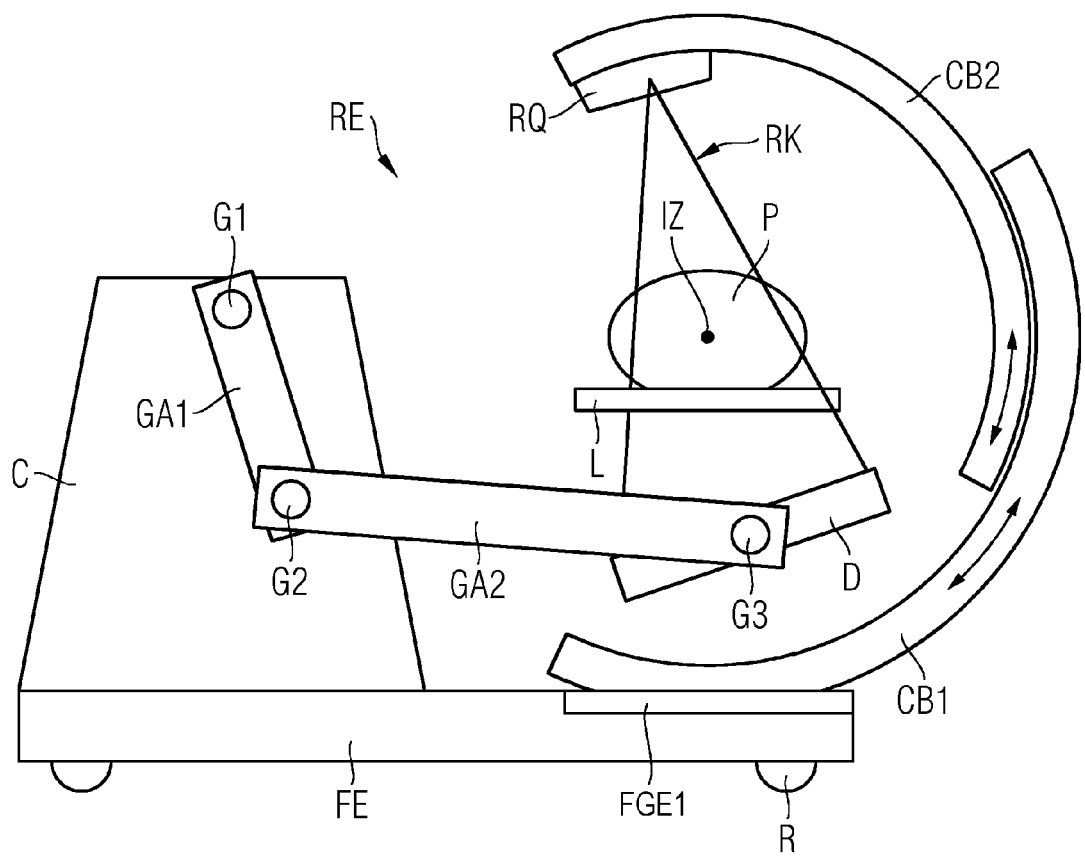
FIG. 3 shows a further side view.

FIGS. 2 and 3 each show possible orientations of the detector D and of the X-ray source RQ of the X-ray device RE. In these illustrations, the detector D is shown positioned to the side of the bed L and positioned below the bed L, respectively. In line with the spatial arrangement of the detector D, the X-ray source RQ is oriented to the side of or above the patient P. The X-ray source RQ moves on an arc of a circle about the patient P or about the bed L.

The first and second arc-shaped positioning elements CB1, CB2 are designed in such a way that they can form at least a half circle about the object P. By means of a movement of the first positioning element CB1 and a tracking movement of the second positioning element CB2, the X-ray source RQ is able to describe a complete circle around the patient P. By means of the indicated trajectory about an isocenter IZ indicated in the patient P, a plurality of 2D X-ray images of the patient P can be taken and, in an image computer unit not shown or described in detail here, can be processed to give slice images and/or a 3D data record. With subsequent processing programs, individual slice images and/or 3D images can then be created from the 3D data record and can be assessed for diagnostic purposes.

Figure 4:
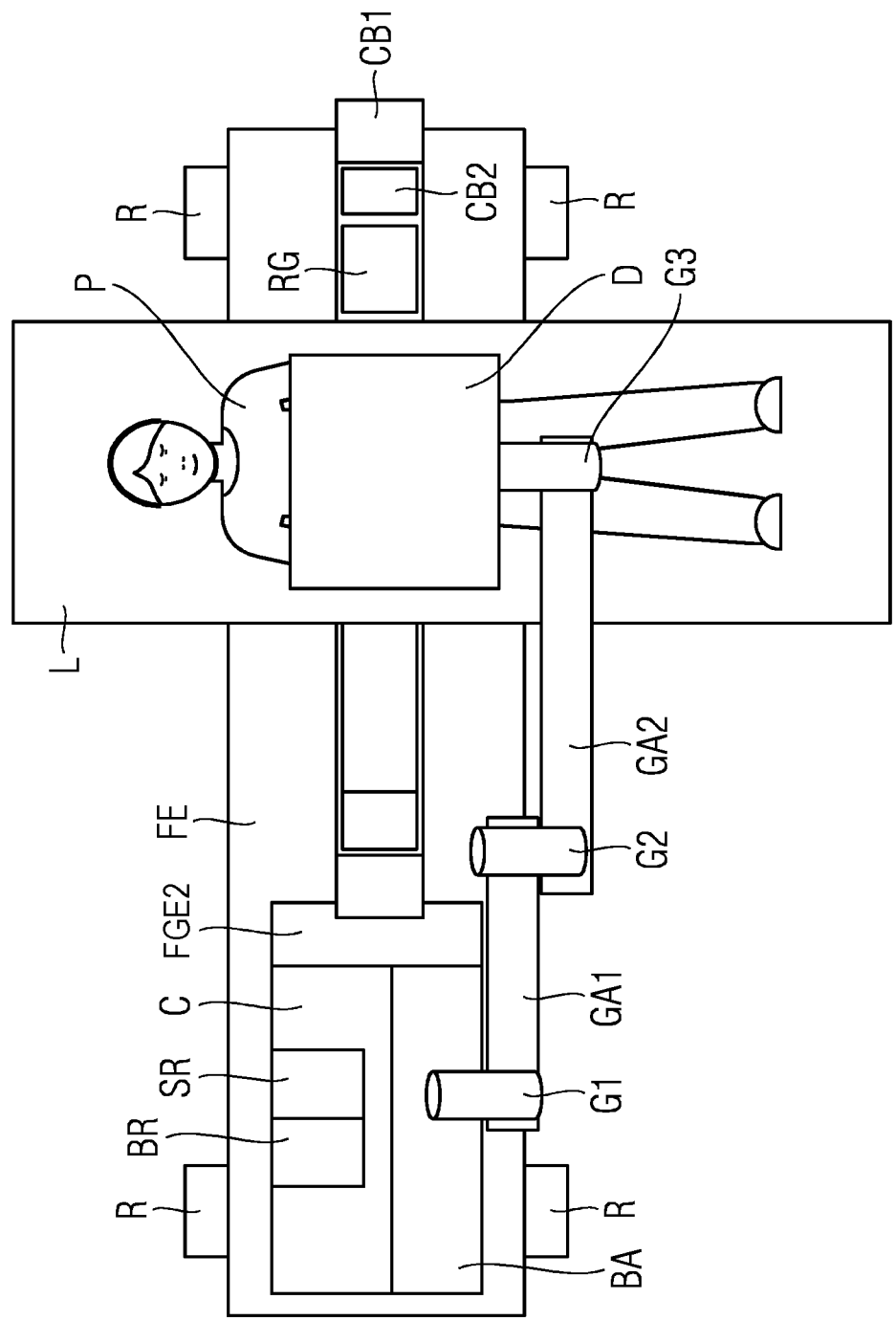
FIG. 4 shows a plan view of the X-ray device.

FIG. 4 shows a plan view of the mobile X-ray device RE. This illustration shows a configuration of the articulated arms GA1, GA2 connected by means of the articulations G1, G2. In this embodiment, the first articulation G1 engages in fastening and driving means BA arranged in the chassis C. The part of the first articulation G1 protruding from the chassis C is connected to the first articulated arm GA1. With this embodiment, a lateral arrangement of the first and second articulated arms GA1, GA2 on the chassis C is shown. The detector D is arranged at the end of the second articulated arm GA2, via a third articulation G3. In this orientation of the detector D, it is positioned above the patient P. This illustration likewise shows that the second positioning element CB is composed of a first arc-shaped positioning element CB1 and of a second arc-shaped positioning element CB2. The second positioning element CB2 engages in guide elements which are formed in the first positioning element CB1.

A positioning of the detector D and the positioning of the X-ray source RQ can take place manually or by motor or partially by motor. For X-ray images, the X-ray source RQ can also be kept stationary, while the beam direction of the X-ray source RQ tracks the trajectory of the detector D. A tracking of the detector D or an orientation of the detector D can take place according to the adjustment of the beam orientation. When a trajectory is determined by the surgical team, this trajectory can be navigated independently and fully electronically with the aid of electric motors. The X-ray source RQ is secured on the inner of two arc-shaped positioning elements CB1, CB2 running one inside the other. By means of the adoptable position of the detector D and of the X-ray source RQ, the patient P can be imaged from a large number of imaging directions. Both arc-shaped positioning elements CB1, CB2 adopt their parked position near the movable unit FE.

By means of a light-beam localizer, the detector D is able to be oriented, on the one hand, and the surgeon or the radiologist, on the other hand, can be shown which region of the patient is being radiated.

LIST OF REFERENCE SIGNS

RE X-ray device
P patient
L bed
D detector
RQ X-ray source
RK X-ray cone
IZ isocenter
C chassis
BA fastening and driving means
SR control computer
BR image computer
GA first positioning unit
GA1 first articulated arm of the first positioning unit
GA2 second articulated arm of the first positioning unit
G1 first articulation
G2 second articulation
G3 third articulation
CB second positioning unit
CB1 first positioning element of the second positioning unit
CB2 second positioning element of the second positioning unit
FE movable unit
FGE1 first guide element FGE2 second guide element
BW1 first directions of movement
BW2 second directions of movement
R rollers/wheels
BWR directions of movement

The invention claimed is:

1. An X-ray device, comprising:
   a detector and a first positioning unit for said detector;
   an X-ray source and a second positioning unit for said X-ray source;
   said first and second positioning units being able, in a course of movements thereof, to perform positioning that is matched to one another;
   said first positioning unit including at least one articulated arm and said second positioning unit having a first arc-shaped positioning element and a second arc-shaped positioning element;
   a movable unit supporting said first and second positioning units, said first and second positioning units being arranged separately from one another on said movable unit, said movable unit including a chassis thereon; and
   said at least one articulated arm connected to said chassis via a first articulation protruding from said chassis, said at least one articulated arm rotatable about said first articulation.

2. The device according to claim 1, wherein said movable unit includes a guide element and said first arc-shaped positioning element is mounted movably and fixably on said movable unit.

3. The device according to claim 1, wherein said second arc-shaped positioning element is mounted fixably on or in said first arc-shaped positioning element.

4. The device according to claim 3, wherein said first and second positioning elements are arranged on top of one another in a rest position.

5. The device according to claim 3, wherein said movable unit supports first and second guide elements, and said first arc-shaped positioning element is mounted movably and fixably on said first and second guide elements between said chassis and said movable unit.

6. The device according to claim 1, wherein said first and second arc-shaped positioning elements are configured to cover a circle segment of more than 180°.

7. The device according to claim 1, wherein said detector is a freely positionable detector and a beam source of said X-ray source is configured to track said freely positionable detector.

8. A method for operating an X-ray device, the method which comprises:
   providing a device according to claim 1, with the at least one articulated arm forming a first positioning unit for the detector and first and second arc-shaped positioning elements forming a second positioning unit for positioning the X-ray source; and
   coordinating a movement of the first positioning unit and of the second positioning unit so that, in a course of a movement of the first and second positioning units, a positioning of the X-ray detector and the X-ray source are matched to one another.

9. An X-ray device, comprising:
   a detector and a first positioning unit for said detector;
   an X-ray source and a second positioning unit for said X-ray source;
   said first and second positioning units being able, in a course of movements thereof, to perform positioning that is matched to one another;
   said first positioning unit including at least one articulated arm and said second positioning unit having a first arc-shaped positioning element and a second arc-shaped positioning element;
   a movable unit supporting said first and second positioning units, said first and second positioning units being arranged separately from one another on said movable unit, said movable unit including a chassis; and
   said at least one articulated arm including a first non-curved arm and a second non-curved arm, said first non-curved arm connected to said chassis via a first articulation proximal to an end of said first non-curved arm, said first non-curved arm rotatable about said first articulation, said second non-curved arm connected between said first non-curved arm and said detector and rotatable about a second articulation connected to said first non-curved arm to change an angle of said second non curved arm relative to said first non-curved arm.

10. The device according to claim 9, wherein said movable unit includes a guide element and said first arc-shaped positioning element is mounted movably and fixably on said movable unit.

11. The device according to claim 9, wherein said second arc-shaped positioning element is mounted fixably on or in said first arc-shaped positioning element.

12. The device according to claim 11, wherein said first and second positioning elements are arranged on top of one another in a rest position.

13. The device according to claim 11, wherein said movable unit supports first and second guide elements, and said first arc-shaped positioning element is mounted movably and fixably on said first and second guide elements between said chassis and said movable unit.

14. The device according to claim 9, wherein said first and second arc-shaped positioning elements are configured to cover a circle segment of more than 180°.

15. The device according to claim 9, wherein said detector is a freely positionable detector and a beam source of said X-ray source is configured to track said freely positionable detector.

16. A method for operating an X-ray device, the method which comprises:
   providing a device according to claim 9, with the at least one articulated arm forming a first positioning unit for the detector and first and second arc-shaped positioning elements forming a second positioning unit for positioning the X-ray source; and
   coordinating a movement of the first positioning unit and of the second positioning unit so that, in a course of a movement of the first and second positioning units, a positioning of the detector and the X-ray source are matched to one another.

* * * * *